(12) United States Patent
Chen et al.

(10) Patent No.: US 7,968,308 B2
(45) Date of Patent: Jun. 28, 2011

(54) ISOLATING HUMAN ANTIBODIES

(75) Inventors: Yiyou Chen, San Jose, CA (US); Dan Chen, Los Altos, CA (US); Anthony G. Day, San Francisco, CA (US); David A. Estell, San Francisco, CA (US); Wei Geng, Hercules, CA (US)

(73) Assignee: Danisco US Inc., Palo Atlo, CA (US)

( * ) Notice: Subject to any disclaimer, the term of this patent is extended or adjusted under 35 U.S.C. 154(b) by 0 days.

(21) Appl. No.: 11/662,752

(22) PCT Filed: Oct. 18, 2005

(86) PCT No.: PCT/US2005/037641
§ 371 (c)(1),
(2), (4) Date: Mar. 24, 2008

(87) PCT Pub. No.: WO2007/001420
PCT Pub. Date: Jan. 4, 2007

(65) Prior Publication Data
US 2008/0268420 A1  Oct. 30, 2008

(51) Int. Cl.
*G01N 33/50* (2006.01)
*C12P 21/08* (2006.01)
(52) U.S. Cl. .................. 435/7.24; 435/70.4; 436/501
(58) Field of Classification Search ................ None
See application file for complete search history.

(56) References Cited

U.S. PATENT DOCUMENTS

| | | |
|---|---|---|
| 4,458,066 A | 7/1984 | Caruthers et al. |
| 4,946,778 A | 8/1990 | Ladner et al. |
| 5,001,056 A * | 3/1991 | Snyder et al. ............ 435/70.21 |
| 5,061,620 A | 10/1991 | Tsukamoto et al. |
| 5,677,136 A | 10/1997 | Simmons et al. |
| 5,750,397 A | 5/1998 | Tsukamoto et al. |
| 6,261,535 B1 | 7/2001 | Thorpe et al. |

FOREIGN PATENT DOCUMENTS

| WO | WO 90/13678 A1 | 11/1990 |
|---|---|---|
| WO | WO2004/102198 | * 11/2004 |

OTHER PUBLICATIONS

Zafiropoulos et al (Journal of Immunological Methods, 1997, vol. 200, pp. 181-190).*

Lindhout et al (The Histochemical Journal, 1995, vol. 27, pp. 167-183).*
Andersson, E. et al., "A tandem repeat of MUC1 core protein induces a weak in vitro immune response in human B cells," *Cancer Immunology, Immunotherapy*, 47(5): 249-256 (1999).
Beaucage, S.L. et al., "Deoxynucleoside phosphoramidites—A new class of key intermediates for deoxypolynucleotide synthesis," *Tetrahedron Lett.*, 22(20):1859-1862 (1981).
Benito, A. et al., "Insertion of a 27 amino acid viral peptide in different zones of *Escherichia coli* β-galactosidase: Effects on the enzyme activity." *FEMS Microbiology Letters* 123:107-112 (1994).
Brown, E.L. et al., "Chemical synthesis and cloning of a tyrosine tRNA gene," In *Recombinant DNA, Methods in Enzymology*, 68:109-151 (1979).
Cole, S.P.C. et al. "The EBV-Hybridoma Technique and its Application to Human Lung Cancer." In *Monoclonal Antibodies and Cancer Therapy*, edited by R.A. Reisfeld et al., pp. 77-96. New York: A.R. Liss, 1985.
Cote, R.J. et al., "Generation of human monoclonal antibodies reactive with cellular antigens," *Proc. Natl. Acad. Sci. U.S.A.*, 80(7):2026-30 (1983).
Goldstein, N.I., "An In Vitro Methodology for the Generation of Activated Human B Cells Producing Antibody to Carcinoembryonic Antigen (CEA)," *J. Cellular Biochem. Supp.*, 14, Part B: 81 (1990).
Goodchild, J., "Conjugates of oligonucleotides and modified oligonucleotides: a review of their synthesis and properties," *Bioconjug. Chem.*, 1(3):65-87 (1990).
Huse, W.D. et al. "Generation of a large combinatorial library of the immunoglobulin repertoire in phage lambda," *Science*, 246:1275-1281 (1989).
Kantor, A.B. et al., "Development of the Antibody Repertoire as Revealed by Single-Cell PCR of FACS-Sorted B-Cell Subsets," *Annals of the New York Academy of Sciences*, 764:224-227 (1995).
Köhler, G. et al., "Continuous cultures of fused cells secreting antibody of predefined specificity," *Nature*, 256:495-497 (1975).
Kozbor, D. et al., "The production of monoclonal antibodies from human lymphocytes," *Immunology Today*, 4(3):72-79 (1983).
Narang, S.A. et al., "Improved phosphotriester method for the synthesis of gene fragments," *Meth. Enzymol.*, 68:90-99 (1979).
Petrarca, C. et al. "Isolation of MUC1-primed B lymphocytes from tumour draining lymph nodes by immunomagnetic beads," *Cancer Immunol. Immunother.*, 47(5):272-277(1999).
Sblattero, D. et al., "A definitive set of oligonucleotide primers for amplifying human V regions," *Immunotechnology* 3(4): 271-278 (1998).
Voso, M.T. et al., "Lack of t(14; 18) Polymerase Chain Reaction-Positive Cells in Highly Purified CD34+ Cells and Their CD19 Subsets in Patients With Follicular Lymphoma," *Blood*, 89(10):3763-3768 (1997).

* cited by examiner

*Primary Examiner* — Karen A Canella

(57) ABSTRACT

The invention is drawn to a method of isolating human antibodies.

2 Claims, 13 Drawing Sheets

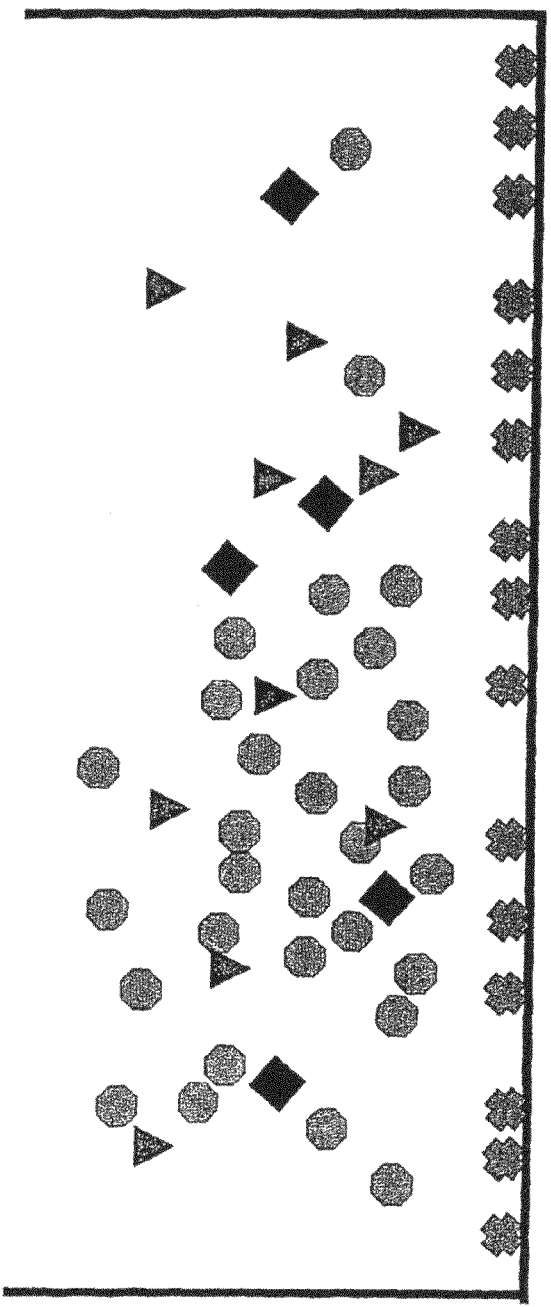

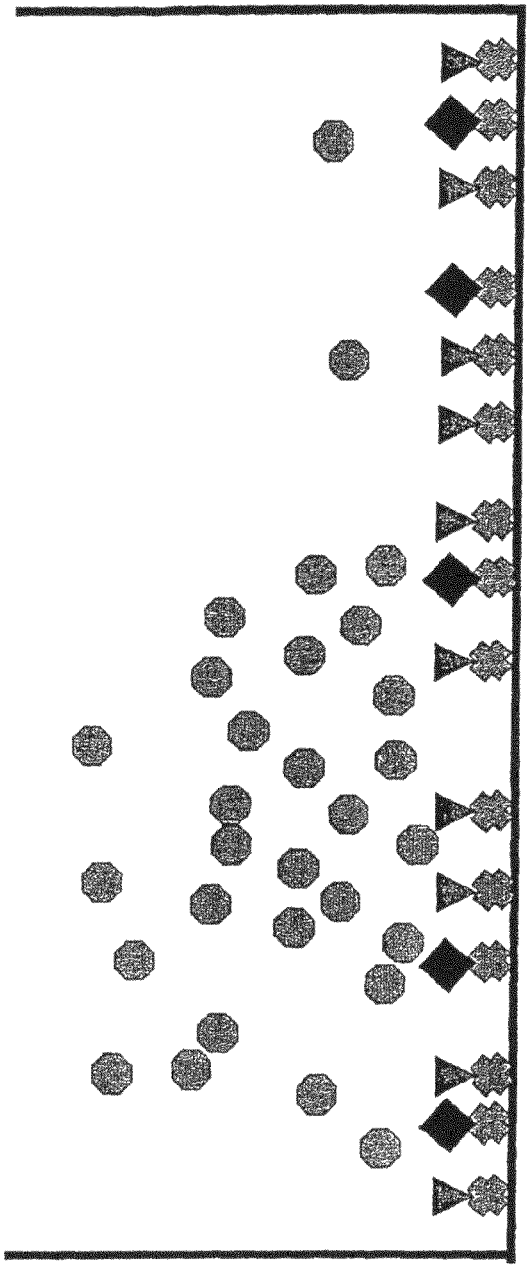

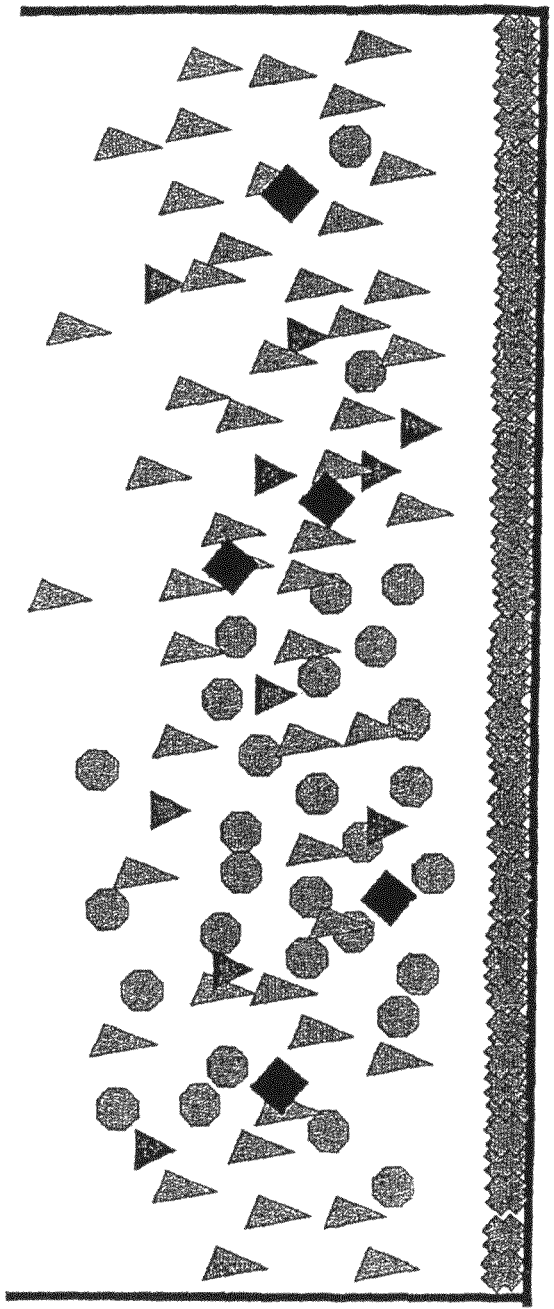

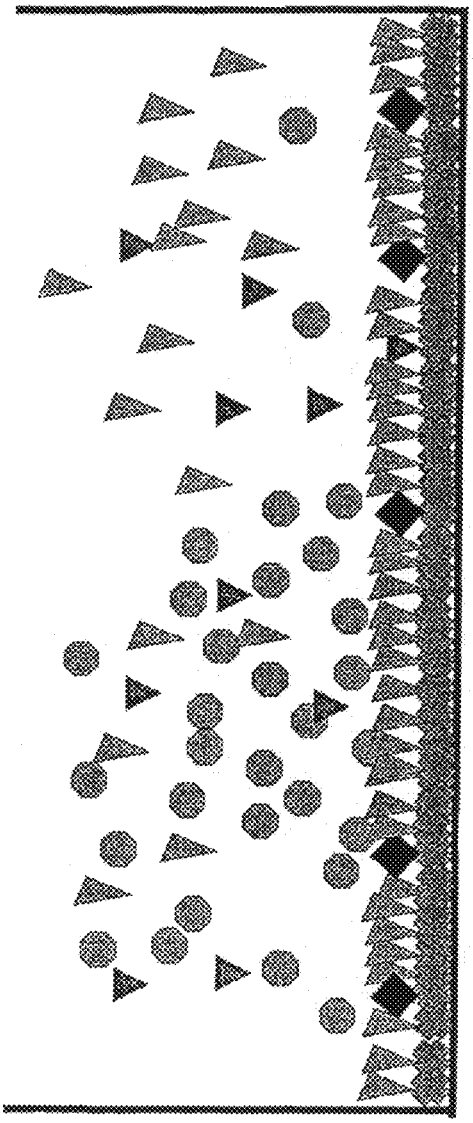

ISOLATING HUMAN ANTIBODIES

FIELD OF THE INVENTION

The present invention provides methods for isolating human antibodies.

BACKGROUND OF THE INVENTION

Monoclonal antibodies have become important pharmaceuticals, largely due to the high affinities and selectivity that are possible to achieve with monoclonals. Since the first development of monoclonal antibodies in the 1970s, the use of monoclonal antibodies specific to disease targets of interest has provided new therapeutic options for treatment of various diseases, including but not limited to cancer and autoimmune diseases.

Although methods for producing and using monoclonal antibodies have improved over time, the methods used to identify new monoclonal antibodies are not robust and reliable. For example, immunization of human Ig transgenic mice does not guarantee a yield of high affinity antibodies. Further, hybridoma generation and screening is tedious and time consuming. Additionally, although antibody phage display offers many advantages over the use of transgenic mice, the screening effort is daunting. In these methods, the library size requirement and the necessity of pairing heavy and light chain genes in their original configuration is time intensive and not guaranteed. Thus, easy methods that facilitate reliable isolation and identification of antibodies are needed.

SUMMARY OF THE INVENTION

The present invention provides methods for isolating human antibodies, comprising: purifying B-cells; contacting B-cells with at least one labeled target at a number of target concentrations to identify a concentration at which a small number of B-cells bind to the target; collecting B-cells bound to the target; and distinguishing, separating and identifying the antibody to which the B-cells have bound the target.

In some preferred embodiments, the B-cells are isolated and purified from human donor blood or bone marrow. In further preferred embodiments, the target is fluorescently labeled and collection occurs through FACS.

In some alternative preferred embodiments, B-cells and target are combined at a number of target concentrations so binding affinity of the antibody may be determined.

In some additional preferred embodiments, the polymerase chain reaction (PCR) is employed to identify the antibody. In some other preferred embodiments, single B-cells are cultured, thereby increasing clonal population.

In some preferred embodiments, at least one labeled target has a low concentration. In some particularly preferred embodiments, the low target concentration is between about 1 micromolar (1e-6M) and about 1 picomolar (1e-12M), while in other particularly preferred embodiments, the low target concentration is between about 1e-7 M and about 1e-11 M.

In some preferred embodiments, at least one labeled target is selected from the group consisting of cancerous cells, cell lines or cell cultures, tumor extracts or cancerous tissues or organs.

In some particularly preferred embodiments, at least one labeled target is an antigen. In some preferred embodiments, the antigen is selected from the group consisting of the cancer antigens Muc-1, Tag72, CEA, CD22, ED-B and FAP.

In some preferred embodiments, the methods further comprise validating the antibody. In some particularly preferred embodiments, validation is accomplished by creating a scFv-enzyme fusion. In some more preferred embodiments, the scFv-enzyme fusion is a scFv-BLA fusion. In some further preferred embodiments, validation is accomplished through a nitrocefin assay.

The present invention also provides methods for isolating human antibodies, comprising the steps of: contacting B-cells with at least one labeled target at a number of target concentrations to identify a concentration at which a small number of B-cells bind to the target; collecting B-cells bound to the target; and distinguishing, separating and identifying the antibody to which the B-cells have bound the target. In some preferred embodiments, the B-cells are isolated and purified from human donor blood or bone marrow. In further preferred embodiments, the target is fluorescently labeled and collection occurs through FACS.

In some alternative preferred embodiments; B-cells and target are combined at a number of target concentrations so binding affinity of the antibody may be determined.

In some additional preferred embodiments, the polymerase chain reaction (PCR) is employed to identify the antibody. In some other preferred embodiments, single B-cells are cultured, thereby increasing clonal population.

In some preferred embodiments, at least one labeled target has a low concentration. In some particularly preferred embodiments, the low target concentration is between about 1 micromolar (1e-6M) to about 1 picomolar (1e-12M), while in other particularly preferred embodiments, the low target concentration is between about 1e-7 M and about 1e-11 M.

In some preferred embodiments, at least one labeled target is selected from the group consisting of cancerous cells, cell lines or cell cultures, tumor extracts or cancerous tissues or organs.

In some particularly preferred embodiments, at least one labeled target is an as antigen. In some preferred embodiments, the antigen is selected from the group consisting of the cancer antigens Muc-1, Tag72, CEA, CD22, ED-B and FAP.

In some preferred embodiments, the methods further comprise validating the antibody. In some particularly preferred embodiments, validation is accomplished by creating a scFv-enzyme fusion. In some more preferred embodiments, the scFv-enzyme fusion is a scFv-BLA fusion. In some further preferred embodiments, validation is accomplished through a nitrocefin assay.

DESCRIPTION OF THE DRAWINGS

FIG. 6 provides a graph showing competitive binding, based on elution, versus retention. FIG. 6A shows B-cell binders suspended in solution, while " FIG. 6 shows binding of three classes of binders to an immobilized target. The Figure is based upon calculations provided and performed throughout the present specification.

FIG. 7 shows the effect of decreasing target concentration. FIG. 7A shows B-cell binders suspended in solution. FIG. 7B shows B-cell binders bound to target; the molecules with the slowest off rate (the two types of molecules with the lowest concentration) are bound.

FIG. 8 shows the effect of adding competitive B-cell binders to a library. FIG. 8A shows B-cell binders suspended in solution. FIG. 8B shows competitive binding, and binders with a high concentration and slow off rate sticking to the target. There are four different types of binders in the library, and all four take the same amount of time to stick to the target, approximately 10 seconds, but each of the three represented binders has a different off-rate. Binders with a 1 minute off rate are represented by octagons; there are 30 such binders represented. Binders with a 10 minute off rate are represented by isosceles and long triangles; there 10 binders represented as an isosceles triangle and 50 binders represented by a long triangle. Binders with a 100 minute off rate are represented by a square tilted 45 degrees; there are 5 such binders represented. Target is shown at the bottom of the Figure as an "X." The Figure shows binding of three classes of binder to an immobilized target when a competitive binder is limiting. This Figure is based upon calculations performed using the methods provided herein.

DESCRIPTION OF THE INVENTION

Figure 1:
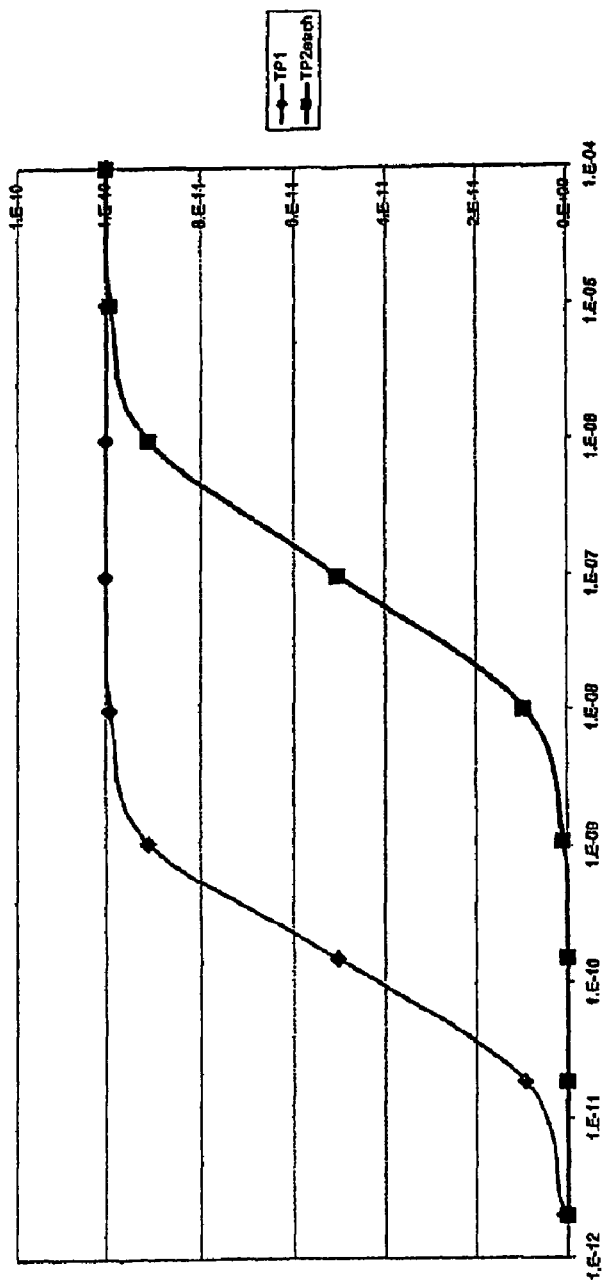
FIG. 1 provides a graph showing competition between B-cells (P1 and P2), both present at a concentration of $1^{-10}$M, with the concentration of target-bound P1 and P2 (TP1 and TP2 respectively) charted as a function of Target concentration ($T_0$). The dissociation constants for P1 and P2 were Kd1=$1^{-10}$ M, Kd2=$1^{-7}$ M. The x-axis shows Target concentration (Molar) and the y-axis shows concentration (Molar) of Target-bound B-cells. As indicated in this Figure, the amount of B-cells bound is a function of disassociation constant and target concentration. This Figure is based upon calculations performed using the methods provided herein.
Figure 2:
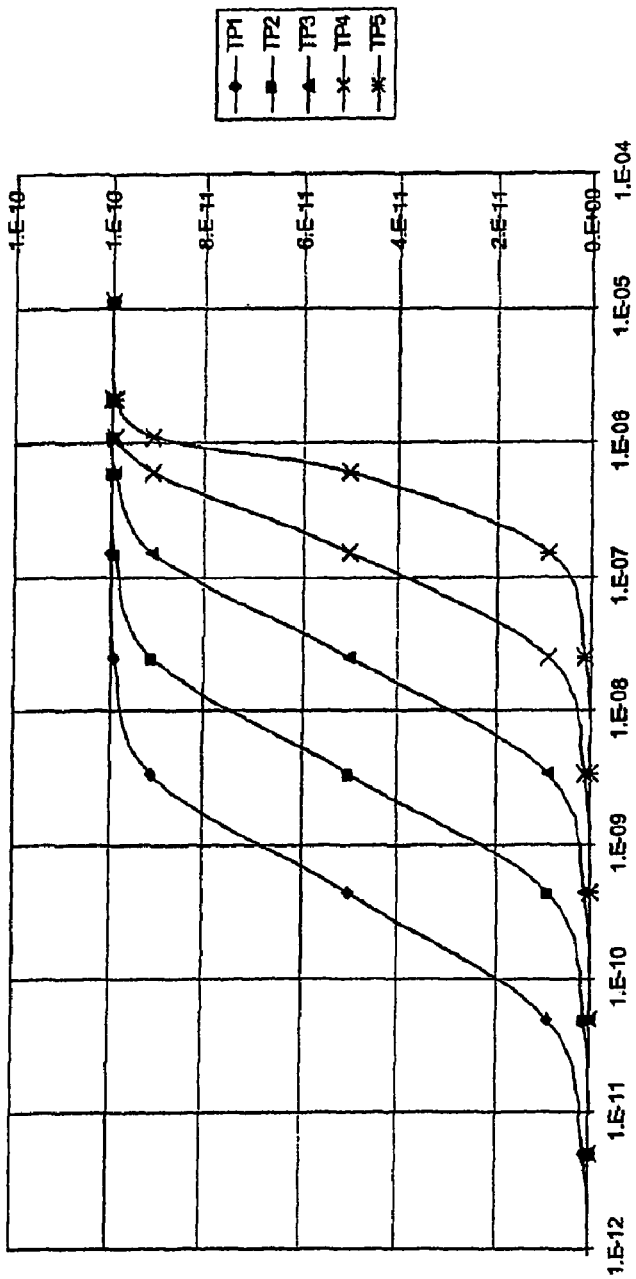
FIG. 2 provides a graph showing the concentration of each bound B-cell, TPi, of a library (each B-cell binder present at a concentration of $1^{-10}$ M) as a function of Target concentration, with 1 binder (P1) Kd=$1^{-12}$ M, 10 binders (P2) at Kd=$1^{-11}$ M, 100 binders (P3) at Kd=$1^{-10}$ M, 1000 binders (P4) at Kd=$1^{-9}$ M, and 10,000 binders (P5) at Kd=$1^{-8}$ M. The x-axis shows Target concentration (Molar) and the y-axis shows concentration (Molar) of Target-bound member. As indicated in this Figure, for members P1 through P5, the amount of B-cell bound is a function of dissociation constant and target concentration of the library. This Figure is based upon calculations performed using the methods provided herein.
Figure 3:
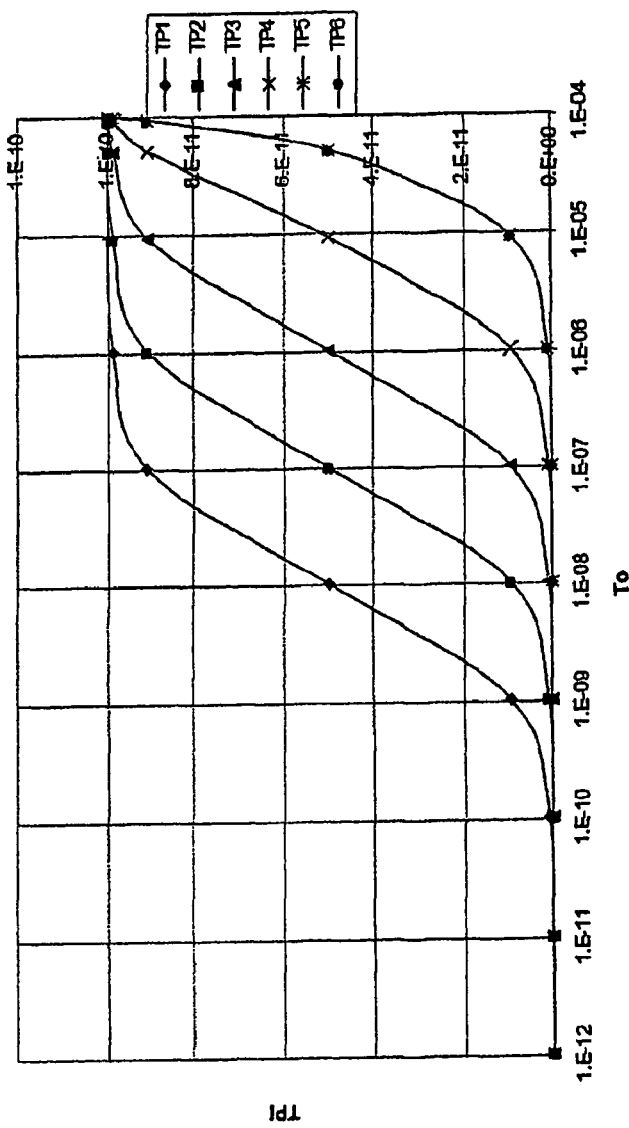
FIG. 3 provides a graph showing the concentration of each bound member, TPi, of a library (each B-cell binder present at a concentration of $1^{-10}$ M) as a function of Target concentration, with 1 binder (P1) Kd=$1^{-12}$ M, 10 binders (P2) at Kd=$1^{-11}$ M, 100 binders (P3) at Kd=$1^{-10}$ M, 1000 binders (P4) at Kd=$1^{-9}$ M, and 10,000 binders (P5) at Kd=$1^{-8}$ M. All conditions were the same as indicated for FIG. 2, except that 1 additional competitive binder (P6) at Kd=$1^{-8}$ M was added at a concentration of $1^{-4}$ M. The x-axis shows Target concentration (Molar) and the y-axis shows concentration (Molar) of Target-bound member. As indicated in this Figure, the amount of B-cell members P1 through P5 bound as a function of the dissociation constant and target concentration of the library. This Figure is based upon calculations performed using the methods provided herein.

The present invention provides methods for isolating human antibodies.

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology*, 2d Ed., John Wiley and Sons, NY (1994); and Hale and Margham, *The Harper Collins Dictionary of Biology*, Harper Perennial, N.Y. (1991) provide those of skill in the art with general dictionaries of many of the terms used in the invention. Additional references widely known to those in the art include Sambrook et al., *Molecular Cloning: A Laboratory Manual*, 2nd ed., Cold Spring Harbor Laboratory Press, New York [1989], and Ausubel et al., *Current Protocols in Molecular Biology*, Greene-Publishing & Wiley Interscience NY (1987; supplemented through 1999).

Although various methods and materials similar or equivalent to those described herein find use in the practice of the present invention, preferred methods and materials are described herein. Accordingly, the terms defined immediately below are more fully described by reference to the Specification as a whole. Also, as used herein, the singular "a," "an," and "the" include the plural reference unless the context clearly indicates otherwise.

Generally, the nomenclature used, and standard laboratory procedures such as cell culture, molecular genetics, and nucleic acid chemistry and hybridization, are well known and commonly employed in the art. Standard techniques are used for recombinant nucleic acid methods, polynucleotide synthesis, microbial culture, cell culture, tissue culture, transformation, transfection, transduction, analytical chemistry, organic synthetic chemistry, chemical syntheses and chemical analysis. Generally, enzymatic reactions and purification and/or isolation steps are performed according to the manufacturers' specifications.

The binding affinity of a B-cell for its target may be described in terms of its dissociation constant (Kd), the concentration needed for 50% effective binding (EC50), and/or the concentration needed for 50% inhibition of binding of another compound that binds to the target (IC50). "Ko" is defined by $k_{off}/k_{on}$. The $k_{off}$ value defines the rate at which the complex breaks apart or separates, while the $k_{on}$ value describes the rate at which the B-cell and target combine to form a complex. Binding affinity terms are sometimes referred to in the art as the kinetic stability of the complex or the ratio of any other measurable quantity that reflects the ratio of binding affinities. Selectivity is defined either by the ratio of binding affinities or of the ratio of off rates (e.g., target molecule Kd/anti-target molecule Kd). Depending on the circumstances, it may be desirable to increase $K_{on}$, decrease $K_{off}$, or both, depending on the application. Thus, it is contemplated that all of these modifications will find use with the present invention.

Figure 7C:
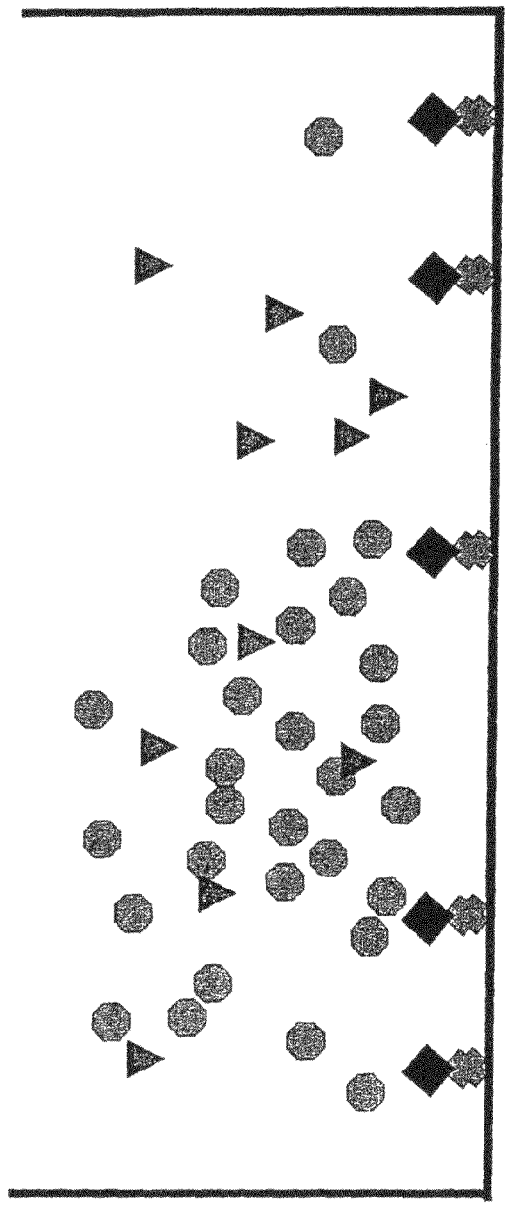
FIG. 7C shows some B-cell binders, only the binders with the slowest off rate (at the lowest concentration) bound to target. There are three different types of binders represented, and all three take the same amount of time to stick to the target, approximately 10 seconds, but each of the three binders has a different off-rate. Binders with a 1 minute off rate are represented by octagons; there are 30 such binders represented. Binders with a 10 minute off rate are represented by a triangle; there are 10 such binders represented. Binders with a 100 minute off rate are represented by a square tilted 45 degrees; there are 5 such binders represented. Target is shown at the bottom of the Figure as an "X." The Figures show binding of three classes of binder to an immobilized target when the amount of the target is limiting. The Figure is based upon calculations provided and performed throughout the present specification.

As used herein, the word "type" refers to a type of B-cells as differentiated by binding affinity (Kd), from another type of B-cells by its binding affinity. For example, in some methods of the present invention which include three different types of binders, three classes of agents that have, roughly, three different binding affinities are included. "Types" are illustrated in FIG. 7, in which there are three different types of binders: 1) those with a one second off rate; 2) those with a ten second off rate; and 3) those with a 100 second off rate.

As used herein, "protein" refers to any composition comprised of amino acids and recognized as a protein by those of skill in the art The terms "protein," "peptide" and polypeptide are used interchangeably herein. Wherein a peptide is a portion of a protein, those skilled in the art understand the use of the term in context. The term "protein" encompasses mature forms of proteins, as well as the pro- and prepro-forms of related proteins. Prepro forms of proteins comprise the mature form of the protein having a prosequence operably linked to the amino terminus of the protein, and a "pre-" or "signal" sequence operably linked to the amino terminus of the prosequence. It is intended that the terms also encompass such sequences as those of antibodies.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine), nonpolar side chains (e.g., alanine, valine, leucine, isoleucine, proline, phenylalanine, methionine, tryptophan, cysteine, glycine), beta-branched side chains (e.g., threonine, valine, isoleucine) and aromatic side chains (e.g., tyrosine, phenylalanine, tryptophan, histidine). Standard three-letter or one-letter amino acid abbreviations, as known in the art, are used herein. Equivalent substitutions may be included within the scope of the claims (e.g., a substitution of an amino acid for another amino acid from the same group).

In some embodiments, the peptides, polypeptides and/or proteins of the invention comprise one or more non-classical amino acids. "Non-classical amino acids" include, but are not limited to the D-isomers of the common amino acids, α-amino isobutyric acid, 4-aminobutyric acid (4-Abu), 2-aminobutyric acid (2-Abu), 6-amino hexanoic acid (Ahx), 2-amino isobutyric acid (2-Aib), 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, "designer" amino acids such as β-methyl amino acids, Cα-methyl amino acids, Nα-methyl amino acids, and amino acid analogs in general.

"Antibody" (Ab) and "immunoglobulin" (Ig) as used herein, refer to defined as a glycoprotein produced by B cells and plasma cells of humans and other animals, that binds with high specificity to an antigen (usually, but not always, a peptide) or a structurally similar antigen, that generated its production. Antibodies may be produced by any of the known methodologies and may be either polyclonal or monoclonal. The term also encompasses chimeric antibodies, humanized antibodies, immunoglobulins or antibody or functional fragments of an antibody that bind to an antigen. Examples of such functional entities include complete antibody molecules, antibody fragments, such as Fv, single chain Fv, complementarity determining regions (CDRs), $V_L$ (light chain variable region), $V_H$ (heavy chain variable region), and any combination of those or any other functional portion of an immunoglobulin peptide capable of binding to target antigen.

The antibodies used in the present invention may be prepared using various immunogens. Various procedures known in the art may be used for the production of polyclonal antibodies. In some embodiments for the production of antibody, various host animals (including, but not limited to rabbits, mice, rats, sheep, goats, etc.) are immunized by injection with the peptide corresponding to a target of interest in the present invention. In some preferred embodiments, the peptide is conjugated to an immunogenic carrier (e.g., diphtheria toxoid, bovine serum albumin (BSA), or keyhole limpet hemocyanin [KLH]). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*Bacille Calmette-Guerin*) and *Corynebacterium parvum*.

For preparation of monoclonal antibodies, any technique that provides for the production of antibody molecules by continuous cell lines in culture may be used (See, e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al. Immunol. Today 4:72 [1983]), and the EBV-hybridoma technique to produce human monoclonal antibodies (See e.g., Cole et al., in *Monoclonal Antibodies and Cancer Therapy*, Alan R. Liss, Inc., pp. 77-96 [1985]). In some particularly preferred embodiments of the present invention, the present invention provides monoclonal antibodies of the IgG class.

In an additional embodiment of the invention, monoclonal antibodies are produced in germ-free animals (See e.g., PCT/US90/02545). According to the invention, human antibodies find use and can be obtained by using human hybridomas (See e.g., Cote et al., Proc. Natl. Acad. Sci. U.S.A. 80:2026-2030 [1983]) or by transforming human B cells with EBV virus in vitro (See e.g., Cole et al., supra).

Techniques described for the production of single chain antibodies (U.S. Pat. No. 4,946,778; herein incorporated by reference) find use in the production of single chain antibodies that specifically recognize a molecule of interest. In some embodiments, the techniques described for the construction of Fab expression libraries (See e.g., Huse et al., Science 246:1275-1281 [1989]) are used to allow rapid and easy identification of monoclonal Fab fragments with the desired specificity.

Antibody fragments which contain the idiotype (antigen binding region) of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

The term "oligonucleotide" as, used herein is defined as a molecule comprised of two or more deoxyribonucleotides or ribonucleotides. The exact size depends upon many factors, which in turn depend on the ultimate function or use of the oligonucleotide. Oligonucleotides can be prepared by any suitable method, including, for example, cloning and restriction of appropriate sequences and direct chemical synthesis by any suitable method known in the art, such as the phosphotriester method (See, Narang et al., Meth. Enzymol., 68:90-99 [1979]); the phosphodiester method (See e.g., Brown et al., Meth. Enzymol., 68:109-151 [1979]); the diethylphosphoramidite method (See, Beaucage et all, Tetrahedron Lett. 22:1859-1862 [1981]), and solid support methods (See e.g., U.S. Pat. No. 4,458,066). Various useful reviews of synthesis methods are known to those in the art (See e.g., Goodchild, 1990, Bioconjugate Chemistry 1(3):165-187 [1990]). The above references are incorporated herein by reference.

The term "low concentration" refers to concentrations of target that are from about 1,000 fold higher to about 10 fold lower than the desired dissociation constant for B-cell binders to the target. Low concentrations may be concentrations, for example, at or below about ten times the desired disassociation constant for binding of the library member to the target. In some embodiments, preferred concentrations are between about 1 micromolar (1e-6M) and about 1 picomolar (1e-12M), preferably any concentration between about 1e-7 and about 1e-11.

The term "normal" refers to an entity in a state that lacks observable and/or detectable abnormalities or deficiencies. Thus, a normal cell is one that conforms with, or adheres to, a typical, standard, pattern of expression, level of expression, consistent with the phenotype and genotype of an unaltered cell of its own type. Conversely, "abnormal" means not typical (i.e., atypical), not usual or regular, not normal. Thus, a diseased cell is an "abnormal" cell type.

The term "target" refers to a substance that is recognized by a B-cell. Any suitable biological surface or non-biological surface finds use in the present invention.

In additional embodiments, the biological surface is a surface of an organ, while in alternative embodiments, the biological surface is the surface of a cell or a tissue. In some further embodiments, the biological surface is a surface of a diseased organ, tissue or cell, while in some alternative embodiments, the biological surface is a surface of a normal or healthy organ, tissue or cell.

In yet further embodiments, the surface is a macromolecule in the interstitial space of a tissue. In additional embodiments, the biological surface is the surface of a microorganism, including but not limited to bacteria, fungi, viruses, parasites (helminths, protozoans, etc.). In some embodiments, the microorganism is an animal pathogen, while in other embodiments, the microorganism is non-pathogenic for humans and/or other animals. Sources of cells and/or tissues include humans, non-human animals, bacteria, fungi, and plants.

Thus, it is contemplated that any biological surface (e.g., cells, tissues, skin, nails, internal organs, external organs, and/or hair) will find use as targets in the present invention. In some embodiments, the cells are human, while in alternative embodiments, the cells are non-human animal cells, bacterial cells, or fungal cells. The term also encompasses cells that contain viruses and/or viral particles. In some embodiments, the cells are hematopoietic cells, cancer cells, or retroviral-mediated transduced cells.

In alternative embodiments, the target is a blood cell, including hematopoietic cells (e.g., hematopoietic stem cells, as well as the various immature cells in the erythrocytic, thromobocytic, and leukocytic lineages. "Blood cells" include but are not limited to hematopoietic cells, erythrocytes, neutrophils, monocytes, platelets, mast cells, eosinophils, basophils, lymphocytes, B cells, T cells, plasma cells, mast cells, macrophages and natural killer cells. In some embodiments, the target is an abnormal blood cell. In some embodiments, the HSC targets have a surface antigen expression profile of $CD34^+ Thy-1^+$ or $CD34^+ Thy-1^+ Lin^-$ ("$Lin^-$" refers to a cell population selected on the basis of the lack of expression of at least one lineage specific marker). Methods for isolating and selecting HSCs are well known in the art (See e.g., U.S. Pat. Nos. 5,061,620, 5,677,136, and 5,750,397, each of which is incorporated herein in its entirety).

In other embodiments, the target is a molecule. In some embodiments, the molecule is an organic molecule. In further embodiments, the molecule is a biological molecule. In additional embodiments, the biological molecule is a cell-associated molecule. In still further embodiments, the cell-associated molecule is associated with the outer surface of a cell. In some embodiments, the cell-associated molecule is part of the extracellular matrix. In some additional embodiments, the cell-associated molecule is a protein. In some embodiments, the protein is a receptor. In additional embodiments, the cell-associated molecule is specific to a particular cell type. In further embodiments, the cell is a diseased and/or abnormal cell. In some preferred embodiments, the diseased cell is a cancer cell. In another embodiment, the diseased cell is an infected cell. Additional molecules that find use as targets in the present invention include, but are not limited to, proteins, peptides, nucleic acids, carbohydrates, lipids, polysaccharides, glycoproteins, hormones, receptors, antigens, antibodies, toxic substances, metabolites, inhibitors, drugs, dyes, nutrients and growth factors.

Non-limiting examples of protein and chemical targets encompassed by the present invention include chemokines and cytokines and their receptors. The term "cytokine" as used herein, refers to any of the numerous factors that exert a variety of effects on cells (e.g., inducing growth, differentiation, and/or proliferation). Non-limiting examples include interleukins (IL), such as IL-2, IL-3, IL-4 IL-6, IL-10, IL-12, IL-13, IL-14 and IL-16; soluble IL-2 receptor; soluble IL-6 receptor; erythropoietin (EPO); thrombopoietin (TPO);

granulocyte macrophage colony stimulating factor (GM-CSF); stem cell factor (SCF); leukemia inhibitory factor (LIF); interferons (e.g., IFN-alpha, -beta, and -gamma); oncostatin M (OM); the immunoglobulin superfamily; tumor necrosis factor (TNF) family, particularly TNF-α; transforming growth factors, (e.g., TGF-alpha and TGF-beta); and IL-1α; and vascular endothelial growth factor (VEGF) family, particularly VEGF (also referred to in the art as VEGF-A), VEGF-B, VEGF-C, VEGF-D and placental growth factor (PLGF). Cytokines are commercially available from several vendors including Amgen (Thousand Oaks, Calif.), Immunex (Seattle, Wash.) and Genentech (South San Francisco, Calif.).

As used herein, the term "tissue" refers to a group or layer of similarly specialized cells which together perform certain specialized functions. In some tissues, cells of only one type are present, while in other tissues, cells of different types are present. The term includes but is not limited to lymphoid, lymphadenoid, adipose, bony, aerolar, cartilaginous, connective, elastic, endothelial, epithelial, fibrous, glandular, gut-associated lymphoid (GALT), indifferent, interstitial, reticular, mesenchymal, myeloid, muscular, nervous, osseous, skeletal, subcutaneous, and other tissue types. As used herein, the term also encompasses modified tissues.

The term "target population" refers to a collection of targets of interest to which a B-cell or B-cell population is exposed. A target population may include a single target or a collection of targets, as described herein. Any collection of biological surfaces, including, but not limited to cells, tissues, skin, nails, and/or hair find use as target populations in the present invention.

In some embodiments, target populations include a group of cancerous cells, cell lines or cell cultures, tumor extracts or cancerous tissues or organs, molecules associated with cancerous cells, cell lines or cell cultures, tumor extracts or cancerous tissues or organs, or cells, cell lines or cell cultures, tissues or organs associated with cancerous cells, cell lines or cell cultures, tumor extracts or cancerous tissues or organs. In some embodiments, target populations include antigens or collections of antigens, themselves.

In some preferred embodiments, the target is a "cancer-related target." The term includes any target that a composition of the invention binds to as part of the diagnosis or detection of a cancer or cancer-associated condition in an organism. For example, the term includes cancerous cells, tissues and/or organs; molecules associated with cancerous cells, tissues or organs; and/or molecules, cells, tissues or organs that are associated with cancerous cells, tissues or organs (e.g., a tumor-bound diagnostic molecule administered to a subject) as well as biopsy samples taken from a subject, or a healthy tissue (e.g., vasculature that is associated with cancerous tissue). Examples of cancer-related targets are provided in U.S. Pat. No. 6,261,535, which is incorporated herein by reference in its entirety. However, it is not intended that the present invention be limited to any specific cancer-related targets. The cancer-related target can be related to any cancer or cancer-associated condition. Examples of types of cancers include, but are not limited to carcinomas, sarcomas, myelomas, leukemias, lymphomas, and mixed type cancers.

In some embodiments, the cancer is a bone cancer. Examples include, but are not limited to Ewing's sarcoma, osteosarcoma, rhabdomyosarcoma and other soft-tissue sarcomas. In other embodiments, the cancer is a neurological cancer, including but not limited to brain tumors, oligodendrogliomas, ependymomas, menengiomas, lymphomas, schwannomas, and medulloblastomas. In additional embodiments, the cancer is breast cancer (e.g., ductal carcinoma in situ in the breast). In further embodiments, the cancer is prostate cancer. In still further embodiments, the cancer is an endocrine system cancer (e.g., adrenal, pancreatic, parathyroid, pituitary and thyroid). In additional embodiments, the cancer is a gastrointestinal cancer, (e.g., anal, colorectal, rectal, oral, linguinal, esophageal, stomach, gall bladder, gastric, liver, pancreatic, large intestine, and small intestine cancers). In further embodiments, the cancer is a gynecological cancer (e.g., cervical, endometrial, uterine, fallopian, gestational trophoblastic disease, choriocarcinoma, ovarian, vaginal and vulvar). In still further embodiments, the cancer is a head and neck cancer (e.g., laryngeal, oropharyngeal, parathyroid and thyroid cancer). In additional embodiments, the cancer is a leukemic cancer (e.g., acute lymphocytic leukemia, acute myelogenous leukemia, chronic lymphocytic leukemia, chronic myelogenous leukemia, hairy cell leukemia and/or a myeloproliferative disorder). In still further embodiments, the cancer is a lung cancer (e.g., mesothelioma, non-small cell lung cancer, and small cell lung cancer). In additional embodiments, the cancer is a lymphoma (e.g., AIDS-related lymphoma, cutaneous T-cell lymphoma, B-cell lymphoma, mycosis fungoides, Hodgkin's disease and non-Hodgkin's disease). In other embodiments, the cancer is a myeloma (e.g., multiple myeloma). In still other embodiments, the cancer is a pediatric cancer (e.g., brain tumor, Ewing's sarcoma, leukemia (e.g., acute lymphocytic leukemia or acute myelogenous leukemia), liver cancer, a lymphoma (e.g., Hodgkin's lymphoma or non-Hodgkin's lymphoma), neuroblastoma, retinoblastoma, sarcoma (e.g., osteosarcoma or rhabdomyosarcoma), and Wilms' Tumor. In still further embodiments, the cancer is a male reproductive cancer, including but not limited to prostate, testicular, epididymal, and penile cancer. In additional embodiments, the cancer is a skin cancer (e.g., cutaneous T cell lymphoma, mycosis fungoides, Kaposi's sarcoma, subcutaneous, or melanoma). In further embodiments, the cancer is thyroid cancer (e.g., papillary, follicular, medullary or anaplastic or undifferentiated thyroid carcinoma). In additional embodiments, the cancer is urinary tract cancers (e.g., bladder, kidney and urethral). In further embodiments, the cancer or cancer-related condition is ataxia-telangiectasia, carcinoma of unknown primary origin, Li-Fraumeni syndrome or thymoma. In still further embodiments, the cancer is metastatic cancer.

In additional embodiments, the cancer-related target is a molecule associated with a cancerous cell or tissue. In some embodiments, the molecule is a tumor or tumor vasculature/stroma antigen, for example, CD20, CD19, CD30, CD3, GD2, Lewis-Y, 72 kd glycoprotein (gp72, decay-accelerating factor, CD55, DAF, C3/C5 convertases), CO17-1A (EpCAM, 17-1A, EGP-40), TAG-72, CSAg-P (CSAp), 45 kd glycoprotein, HT-29 ag, NG2, A33 (43 kd gp), 38 kd gp, MUC-1, CEA, EGFR (HER1), HER2, HER3, HER4, HN-1 ligand, CA125, syndecan-1, Lewis X, FAP stromal Ag (fibroblast activation protein), EDG receptors (endoglin receptors), ED-B, laminin-5 (gamma2), cox-2 (+LN-5), PgP (P-glycoprotein), alphaVbeta3 integrin, alphaVbeta5 integrin, uPAR (urokinase plasminogen activator receptor), endoglin (CD105), GD2, aminopeptidase, tenascin-C, NG-2, TEM1, TEM8, annexin, folate receptor osteopontin (EDG 1,3), p97 (melanotransferrin), farnesyl transferase or a molecule in an apoptotic pathway (e.g., a death receptor, fas, caspase or bcl-2) or a lectin.

The present invention also finds use with a wide variety of molecule targets. Suitable target molecules include, but are not limited to, proteins, peptides, nucleic acids, carbohydrates, lipids, polysaccharides, glycoproteins, hormones, receptors, antigens, antibodies, viruses, pathogens, toxic substances, metabolites, inhibitors, drugs, dyes, nutrients, growth factors, cells or tissues.

Other protein and chemical targets include, but are not limited to: immunoregulation modulating proteins, such as soluble human leukocyte antigen (HLA, class I and/or class II, and non-classical class I HLA (E, F and G)); surface proteins, such as soluble T or B cell surface proteins; human serum albumin; arachadonic acid metabolites, such as prostaglandins, leukotrienes, thromboxane and prostacyclin; IgE, auto or alloantibodies for autoimmunity or allo- or xenoimmunity; Ig Fc receptors or Fc receptor binding factors; G-protein coupled receptors; cell-surface carbohydrates; angiogenesis factors; adhesion molecules; ions, such as calcium, potassium, magnesium, aluminum and iron; fibril proteins, such as prions and tubulin; enzymes, such as proteases, aminopeptidases, kinases, phosphatases, DNAses, RNAases, lipases, esterases, dehydrogenases, oxidases, hydrolases, sulphatases, cyclases, transferases, transaminases, carboxylases, decarboxylases, superoxide dismutase and their natural substrates or analogs; hormones and their corresponding receptors, such as follicle stimulating hormone (FSH), leutinizing hormone (LH), thyroxine (T4 and T3), apolipoproteins, low density lipoprotein (LDL), very low density lipoprotein (VLDL), cortisol, aldosterone, estriol, estradiol, progesterone, testosterone, dehydroepiandrosterone (DHBA) and its sulfate (DHEA-S); peptide hormones, such as renin, insulin, calcitonin, parathyroid hormone (PTH), human growth hormone (hGH), vasopressin and antidiuretic hormone (AD), prolactin, adrenocorticotropic hormone (ACTH), LHRH, thyrotropin-releasing hormone (THRH), vasoactive intestinal peptide (VIP), bradykinin and corresponding prohormones; catechcolamines such as adrenaline and metabolites; cofactors including atrionatriutic factor (AdF), vitamins A, B, C, D, E and K and serotonin; coagulation factors, such as prothrombin, thrombin, fibrin, fibrinogen, Factor VIII, Factor IX, Factor XI and von Willebrand factor; plasminogen factors, such as plasmin, complement activation factors, LDL and ligands thereof and uric acid; compounds regulating coagulation, such as hirudin, hirulog, hementin, heparin and tissue plasminogen activator (TPA); nucleic acids for gene therapy; enzyme antagonists; compounds that bind ligands, such as inflammation factors and receptors and other proteins that bind to one or more of the preceding molecules.

Additional chemical targets include without limitation drugs, especially drugs subject to abuse, such as *cannabis*, heroin and other opiates, phencyclidine (PCP), barbiturates, cocaine and its derivatives and benzadiazepine; toxins, such as heavy metals like mercury and lead, arsenic and radioactive compounds; chemotherapeutic agents, such as paracetamol, digoxin and free radicals; bacterial toxins, such as lipopolysaccharides (LPS) and other gram negative toxins, *Staphylococcus* toxins, toxin A, tetanus toxins, diphtheria toxin, and pertussis toxins; plant and marine toxins; snake and other venoms, virulence factors, such as aerobactins, toxins, proteins, etc.; infectious viruses, such as hepatitis, cytomegalovirus (CMV), herpes simplex viruses (e.g., HSV types 1, 2 and 6), Epstein-Barr virus (EBV), varicella zoster virus (VZV), human immunodeficiency viruses (e.g., HIV-1, -2) and other retroviruses, adenoviruses, rotaviruses, influenzae, rhinoviruses, parvoviruses, rubella, measles virus, polio, pararmyxoviruses, papovaviruses, poxviruses, arboviruses, flaviviruses, arenaviruses, rabies virus, caliciviruses, astroviruses, rotaviruses, and picornaviruses; prions; plasmodia tissue factor, protozoans, including amebae (e.g., *Entamoeba histolytica*), filariae (e.g., *Wuchereria*), *Plasinodium, Giardia, Leishmania, Cryptosporidium, Sarcocystis, Babesia,
Trypanosoma*, and *Toxoplasma*; helminths (e.g., trematodes, cestodes and nematodes); bacteria, including aerobic, anaerobic and facultative bacteria responsible for sepsis, nosocomial, and other infections (e.g., *E. coli, Acinetobacter, Pseudomonas, Proteus, Klebsiella, Staphylococcus, Streptococcus, Neisseria*, mycobacteria, *Legionnella, Clostridium, Mycoplasma, Treponema, Chlamydia, Rickettsia, Bartonella*, etc.) and fungi (e.g., *Candida, Pneumocystis, Aspergillus, Trichosporum, Microsporum, Pichnia, Coccidioides, Blastomyces, Histoplasina, Cryptococcus*, etc.). Indeed, it is not intended that the present invention be limited to any particular target, as any target that can be bound (i.e., to form a bound target) finds use in the present invention).

In further embodiments, the target is a plant or plant-derived material. In some embodiments, the target is wood, while in other embodiments, the target is a non-woody plant. It is intended that the present invention encompass any plant and/or plant-derived material.

In some embodiments, the target is an enzyme such as proteases, aminopeptidases, kinases, phosphatases, DNAses, RNAases, lipases, esterases, dehydrogenases, oxidases, hydrolases, sulphatases, cellulases, cyclases, transferases, transaminases, carboxylases, decarboxylases, superoxide dismutase, and their natural substrates or analogs. Particularly preferred enzymes include hydrolases, particularly alpha/beta hydrolases; serine proteases, such as subtilisins, and chymotrypsin serine proteases; cellulases and lipases.

As used herein, the term "molecule" refers to target molecules (e.g., an antigen or a ligand). Suitable agent, target molecules and anti-target molecules include, but are not limited to, proteins, peptides, nucleic acids, carbohydrates, lipids, polysaccharides, glycoproteins, hormones, receptors, antigens, antibodies, viruses, pathogens, toxic substances, metabolites, inhibitors, drugs, dyes, nutrients, growth factors, cells or tissues.

The present invention provides methods for isolating human antibodies, comprising the steps of: purifying B-cells; contacting the purified B-cells with at least one labeled target at a number of different target concentrations, in order to identify a concentration at which a small number of B-cells bind to the target; collecting B-cells bound to the target and distinguishing, separating and identifying the target to which the B-cells have bound.

In some preferred embodiments, B-cells are isolated and purified from human donor blood or bone marrow. In some additional preferred embodiments, the target is, fluorescently labeled and collection of bound B-cells and targets (i.e., B-cell/target complex) is accomplished using methods such as FACS (fluorescence-activated cell sorting).

In some preferred embodiments, B-cells and the target are combined at a number of target concentrations, under conditions such that the binding affinity of the antibody is observable. In some particularly preferred embodiments, the preferred target concentrations are calculated, as described in the Examples and as illustrated in the Figures.

In some preferred embodiments, the target has a low concentration. In some of these preferred embodiments, the low concentration is between about 1 micromolar (1e-6M) and about 1 picomolar (1e-12M). In some more particularly preferred embodiments, the target concentration is between about 1e-7 M and about 1e-11 M.

In some alternative preferred embodiments, a suitable amplification method is used to identify the target/B-cell complex. In some further preferred embodiments, single B-cells are cultured, in order to increase the clonal population.

As indicated above, any suitable target or target population finds use in the present invention. In addition, any suitable biological surface or non-biological surface finds use in the present invention.

In some particularly preferred embodiments, the methods further comprise the step of validating the identified antibody. In some preferred embodiments, validation is accomplished by creating a scFv-enzyme fusion, subjecting the fusion to a binding assay with the original target, and then assaying the fusion for enzymatic activity. Standard assays are well known to one skilled in the art and any suitable assay finds use in the present invention. However, in some preferred embodiments, the enzyme is a beta-lactamase ("BLA"). As used herein, "beta-lactamase" refers to any enzyme that breaks down beta lactam rings (i.e., a heteroatomic ring structure comprising three carbon atoms and one nitrogen atom). Beta lactam rings are components of several antimicrobials, so including but not limited to penicillin, cephalosporin, and other related compounds. In some preferred embodiments, the beta-lactamase of the present invention is native enzyme, while in some other preferred embodiments, the beta-lactamase of the present invention is recombinant. In some additionally preferred embodiments, the beta-lactamases of the present invention are modified.

Examples of specific BLAs that find use in the present invention include, but are not limited to, Class A, B, C, or D β-lactamase and β-galactosidase (See e.g., Benito et al., *FEMS Microbiol. Lett.* 123:107 [1994]).

In some preferred embodiments, binding is confirmed by measuring beta-lactamase activity after antibody binding of the fusion. In some preferred embodiments, activity is measured using the nitrocefin assay known in the art (See e.g., U.S. patent application Ser. No. 10/022,097, incorporated herein by reference).

The present invention also provides methods for isolating human antibodies, comprising the steps of: contacting B-cells with at least one labeled target at a number of target concentrations to identify a concentration at which a small number of B-cells bind to the target; collecting B-cells bound to the target; and distinguishing, separating and identifying the antibody to which the B-cells have bound.

In some preferred embodiments, B-cells are isolated and purified from human donor blood or bone marrow. In some additional preferred embodiments, the target is fluorescently labeled and collection of bound B-cells and targets (i.e., B-cell/target complex) is accomplished using methods such as FACS (fluorescence-activated cell sorting).

In some preferred embodiments, B-cells and the target are combined at a number of target concentrations, under conditions such that the binding affinity of the antibody is observable. In some particularly preferred embodiments, the preferred target concentrations are calculated, as described in the Examples and illustrated in the Figures.

In some preferred embodiments, the target has a low concentration. In some of these preferred embodiments, the low concentration is between about 1 micromolar (1e-6M) and about 1 picomolar (1e-12M). In some more particularly preferred embodiments, the target concentration is between about e-7 M and about 1e-11 M.

In some alternative preferred embodiments, a suitable amplification method is used to identify the target/B-cell complex. In some further preferred embodiments, single B-cells are cultured, in order to increase the clonal population.

EXPERIMENTAL

The following examples serve to illustrate certain preferred embodiments and aspects of the present invention and are not to be construed as limiting the scope thereof.

In the experimental disclosure which follows, the following abbreviations apply: sd and SD (standard deviation); M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml (milliliters); μl (microliters); cm (centimeters); mm (millimeters); μm (micrometers); nm (nanometers); LF (lethal factor); ° C. (degrees Centigrade); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); PBS (phosphate buffered saline); g (gravity); OD (optical density); CPM and cpm (counts per minute); rpm (revolutions per minute); Dulbecco's phosphate buffered solution (DPBS); HEPES (N-[2-Hydroxyethyl]piperazine-N-[2-ethanesulfonic acid]); HBS (HEPES buffered saline); SDS (sodium dodecylsulfate); Tris-HCl (tris[Hydroxymethyl]aminomethane-hydrochloride); 2-ME (2-mercaptoethanol); EGTA (ethylene glycol-bis(β-aminoethyl ether) N,N,N',N'-tetraacetic acid); EDTA (ethylenediaminetetracetic acid); Abbott (Abbott Laboratories, Abbott Park, Ill.); Ambion (Ambion, Austin, Tex.); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Piscataway, N.J.); Pierce (Pierce Biotechnology, Rockford, Ill.); Pharmingen (Pharmingen, San Diego, Calif.); Roche (Roche Diagnostics Corporation, Indianapolis, Ind.); SynPep (SynPep, Corp., Dublin, Calif.); Miltenyi Biotec (Miltenyi Biotec, Bergisch Gladbach, Germany); Bachem (Bachem Biosciences, King of Prussia, Pa.); DNA 2 (DNA 2, Menlo Park, Calif.); Qiagen (Qiagen, Inc., Valencia, Calif.); and Stratagene (Stratagene, La Jolla, Calif.).

In the experiments which follow, the B-cells used were primary human CD19$^+$ B cells isolated from human peripheral blood mononuclear cells (PBMCs) with the MACS separation system according to the manufacturer's instructions (human CD19 MicroBeads; Miltenyi Biotec).

Target proteins were labeled with FITC using the EZ-Label Fluorescein Isothiocyanate Protein Labeling Kit according to the manufacturer's instructions (Pierce, Rockford, Ill., U.S.A.).

Target-specific B-cells were selected using FACS by staining magnetically isolated B-cells with PE-conjugated anti-CD19 antibody (Pharmingen) and FITC-conjugated target proteins at various concentrations (0.1-10 nM) for 30 minutes or overnight at 4° C. CD19-PE and target-FITC double positive cells were sorted into 96-well cell culture plates containing Cell Lysis Buffer (Ambion) at single cell per well density by FACS. Sorted cells were subjected to RT-PCR cloning procedures, as known in the art, or stored at −80° C. for later use.

Example 1

Design of Vh and Vl Primer Sets

In this Example, methods used to design Vh and Vl primer sets are described. Two sets of degenerate oligonucleotide primers for amplifying all functional human variable regions (Vh and Vl) were designed based on information from literature and public sequence databases (See, Table 1; See also, Sblattero and Bradbury, Immunotechnol., 3:271-278 [1998]).

The forward (5') primers (BPF168-187) were located in the first 20-23 nucleotides of framework one of the V genes (See, Sblattero and Bradbury, supra). The reverse (3') primers (BPF154-BPF167) were located at the 5' end of the constant regions and were designed based on sequences from public databases.

TABLE 1

SEQUENCES

| Sequence Name | Sequence | SEQ ID NO: |
|---|---|---|
| BPF154:hukappaC rt 425-403 J00241 | GTTATTCAGCAGGCACACAACAG | SEQ ID NO: 1 |
| BPF155:huKappaC rev 375-352 J00241 | CAGATGGCGGGAAGATGAAGACAG | SEQ ID NO: 2 |
| BPF156:hIGLC rt | AGTGTGGCCTTGTTGGCTTG | SEQ ID NO: 3 |
| BPF157:hIGLC rev | AGCTCCTCAGAGGAGGGYGGGAAC | SEQ ID NO: 4 |
| BPF158:hIGCL rev2 | AGGAGGGYGGGAACAGAGTGACCG | SEQ ID NO: 5 |
| BPF159:huIgGC1rt primer 91-70 | AGTCCTTGACCAGGCAGCCCAG | SEQ ID NO: 6 |
| BPF160:huIgGC1 rev 68-45 | GCSGCTGTGCYCYCRGAGGTGCTC | SEQ ID NO: 7 |
| BPF161:huIgGC1 rev 29-6 | AGGGGGAAGACSGATGGGCCCTTG | SEQ ID NO: 8 |
| BPF162:huIgM rt 78-57 | CAACGGCCACGGTGCTCGTATC | SEQ ID NO: 9 |
| BPF163:huIgM rev 53-30 | CGGGGAATTCTCACAGGAGACGAG | SEQ ID NO: 10 |
| BPF164:huIgM rev 27-4 | GGAAAAGGGTTGGGGCGGATGCAC | SEQ ID NO: 11 |
| BPF165:huIgD rt 232-213 K02875 | CCATGTACCAGGTGACAGTC | SEQ ID NO: 12 |
| BPF166:huIgDC1 rev 155-132 K02875 | TTTGGGTGTCTGCACCCTGATATG | SEQ ID NO:13 |
| BPF167:huIgDC1 rev 126-103 K02875 | GAACACATCCGGAGCCTTGGTGGG | SEQ ID NO:14 |
| BPF168:VH4BACK | CAGGTGCAGCTGCAGGAGTCSG | SEQ ID NO: 15 |
| BPF169:VH5BACK | CAGGTACAGCTGCAGCAGTCA | SEQ ID NO: 16 |
| BPF170:VH6BACK | CAGGTGCAGCTACAGCAGTGGG | SEQ ID NO: 17 |
| BPF171:VH10BACK | GAGGTGCAGCTGKTGGAGWCY | SEQ ID NO: 18 |
| BPF172:VH12BACK | CAGGTCCAGCTKGTRCAGTGTGG | SEQ ID NO: 19 |
| BPF173:VH14BACK | CAGRTCACCTTGAAGGAGTCTG | SEQ ID NO: 20 |
| BPF174:VH22BACK | CAGGTGCAGCTGGTGSARTCTGG | SEQ ID NO: 21 |
| BPF175:VK1BACK | GACATCCRGDTGACCCAGTCTCC | SEQ ID NO: 22 |
| BPF176:VK2BACKts | GAAATTGTRWTGACRCAGTCTCC | SEQ ID NO: 23 |
| BPF177:VK9BACK | GATATTGTGMTGACBCAGWCTCC | SEQ ID NO: 24 |
| BPF178:VK12BACK | GAAACGACACTCACGCAGTCTC | SEQ ID NO: 25 |
| BPF179:VL1BACK | CAGTCTGTSBTGACGCAGCCGCC | SEQ ID NO: 26 |
| BPF180:VL3BACK | TCCTATGWGCTGACWCAGCCAC | SEQ ID NO: 27 |
| BPF181:VL38BACK | TCCTATGAGCTGAYRCAGCYACC | SEQ ID NO: 28 |
| BPF182:VL4BACK | CAGCCTGTGCTGACTCARYC | SEQ ID NO: 29 |
| BPF183:VL78BACK | CAGDCTGTGGTGACYCAGGAGCC | SEQ ID NO: 30 |
| BPF184:VL9BACK | CAGCCWGKGCTGACTCAGCCMCC | SEQ ID NO: 31 |
| BPF185:VL11BACK | TCCTCTGAGCTGASTCAGGASCC | SEQ ID NO: 32 |
| BPF186:VL13BACK | CAGTCTGYYCTGAYTCAGCCT | SEQ ID NO: 33 |
| BPF187:VL15BACK | AATTTTATGCTGACTCAGCCCC | SEQ ID NO: 34 |
| hu beta actin rev | TGTGTTGGCGTACAGGTCTTTG | SEQ ID NO: 35 |
| hu beta actin for | GGGAAATCGTGCGTGACATTAAG | SEQ ID NO: 36 |

Example 2

Cloning of Vh and Vl cDNA from Sorted, Target-Specific B Cells by RT-PCR

In this Example, methods for cloning Vh and Vl cDNA are described. First, cDNA is prepared from selected, antigen-specific single B cells by RT-PCR using the Cells-to-cDNA™ II kit with random hexamers (Ambion). Next, Vh and Vl genes are independently amplified with the Vh and the Vl primer sets using the sequences in Table 1 as templates.

Example 3

Generation of scFv-BLA Fusion Constructs

In this Example, methods for generation of scFv-BLA fusion constricts are described. Amino acid sequences of Vh and Vl genes are obtained by sequencing gel-purified PCR products. The synthetic scFvs are designed with standard (G4S)$_3$ (15 aa) linker in between Vh and Vl: Vh-15aa-Vl, flanked with restriction enzyme sites for cloning purposes. In some experiments, constructs are ordered from commercial suppliers (e.g., DNA 2.0), who can synthesize and clone the molecules into one or more suitable vectors (e.g., pDrive Cloning Vector (Qiagen)). The scFv gene in the construct is isolated via restriction enzyme digestion, gel purified and subcloned into an *E. coli* expression vector, which allows expression of scFv in a beta-lactomase fusion protein.

Example 4

Validation of Fusion Proteins

In this Example, methods for validating fusion proteins are provided. Candidate scFvs are validated using suitable ELISA methods and reagents, as known in the art. Plasmids containing scFv-BLA fusion constructs are transformed into *E. coli*. After culturing, bacterial cells are lysed with B-Per reagent (Pierce). Lysate is added to a 96-well plate pre-coated with the original target protein. Positive BLA fusion proteins are screened using a suitable assay (e.g., the nitrocefin (BLA substrate) assay).

Example 5

Competition Among Binders in Libraries

In this Example, methods to calculate competition between binders in libraries are provided. The following designations are used herein: for a library L of n members, let $T^o$=total amount of target, T=unbound target, $P_i$=unbound library member I, $P_i^o$=total amount of library member I, $K_D^i$=dissociation constant for $P_i$ with T, $TP_i$=complex of $P_i$ with T, $k_{on}^i$=second order association rate constant, $k_{on}^i$=1st order dissociation rate constant.

If we assume: 1) steady state binding is reached; 2) each target has one binding site which binds only one member; and 3) each member has the same second order association rate constant, then the following equation represents competition among library members:

The on rate may be calculated as follows:

$$d(TP_i)/dt = k_{on}^i(T)(P_i)$$

The off rate may be calculated as follows:

$$-d(TP_i)/dt = k_{off}^i(TP_i)$$

At a steady state, the following applies:

$$d(TP_i)/dt = -d(TP_i)/dt$$

$$k_{on}^i(T)(P_i) = k_{off}^i(TP_i)$$

$$k_{off}^i/k_{on}^i = (T)(P_i)/(TP_i) = K_D^i$$

In a library with n members that bind to the target, the concentration of free target is:

$$T = T^o - TP_1 - TP_2 - TP_3 \ldots -TP_n$$

For each member $P_i$:

$$K_D^i = (T)(P_i)/(TP_i)$$

$$T = (TP_i/P_i)K_D^i$$

In the library L, there will be one tightest binding member—call that member $P_1$. The ratio of bound $P_1$ to free $P_1$ as a function of T is:

$$T = (TP_1/P_1)K_D^1$$

since T is the concentration of free target, for any other member $P_i$ of the library:

$$T = (TP_i/P_i)K_D^i$$

For each member Pi of the library, the bound over free ratio $(TP_i/P_i)$ relative to that of the tightest binder $(TP_1/P_1)$ is given by:

$$(TP_i/P_i)K_D^i = (TP_1/P_1)K_D^1$$

$$(TP_i/P_i) = (TP_1/P_1)K_D^1/K_D^i$$

For any member i of the library, the bound to free ratio $(TP_i/P_i)$ relative to that of $P_1$ is directly proportional to the ratio of the two dissociation constants:

$$\text{Let } x = (TP_1/P_1); r_i^1 = K_D^1/K_D^i$$

$$TP_1/P_1^o = (TP_1/P_1)/(1+(TP_1/P_1)) = x/(1+x)$$

$$TP_i/P_i^o = (TP_i/P_i)/(1+(TP_i/P_i))$$

$$TP_i/P_i^o = r_i^1 \cdot x/(1+r_i^1 \cdot x)$$

The ratio of bound member i $(TP_i)$ to bound member 1 $(TP_1)$ is:

$$TP_i/TP_1 = (1+x) \cdot r_i^1 \cdot x \cdot P_i^o/x \cdot (1+r_i^1 \cdot x) \cdot P_1^o$$

$$= (1+x) \cdot r_i^1 \cdot P_i^o/(1+r_i^1 \cdot x) \cdot P_1^o$$

$$= (1+x) \cdot P_i^o/((1/r_i^1)+x) \cdot P_1^o$$

$$TP_i/TP_1 = (1+x) \cdot P_i^o/((1/r_i^1)+x) \cdot P_1^o$$

$$T = (TP_1/P_1)K_D^1 = (x)K_D^1$$

As $T^o$ approaches 0; T approaches 0 and x approaches 0
As $T^o$ approaches ∞; T approaches ∞ and x approaches ∞

$$TP_i/TP_1 = (1+x) \cdot P_i^o/((1/r_i^1)+x) \cdot P_1^o$$

Figure 4:
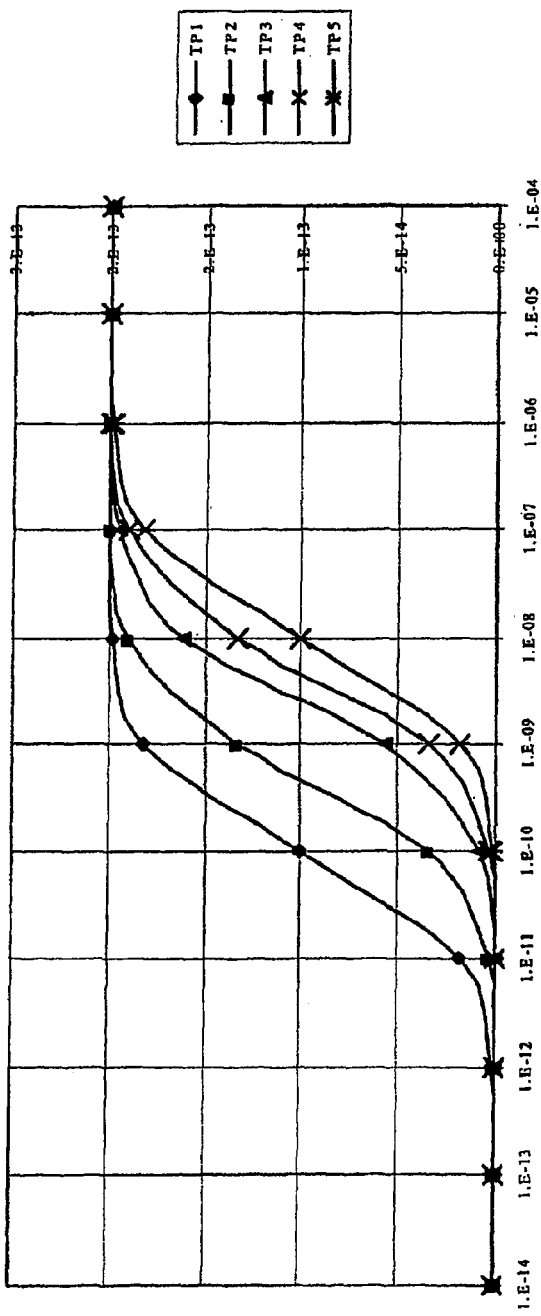
FIG. 4 provides a graph showing bound B-cell concentration verses target concentration. The Figure shows concentration of each bound B-cell binder, TPi, of a library (each member present at a concentration of $1^{-13}$ M) with 1 binder (P1) at Kd=$1^{-10}$ M, 5 binders (P2) at Kd=$5^{-10}$ M, 25 binders (P3) at Kd $2.5^{-9}$ M, 50 binders (P4) at Kd=$5^{-9}$ M, and 100 binders (P5) at Kd=$1^{-8}$ M (and no additional binders). The x-axis shows Target concentration (Molar) and the y-axis shows concentration (Molar) of Target-bound member. The Figure shows the amount of library member bound as a function of dissociation constant and target concentration for a typical library with members P1 through P5. This Figure is based upon calculations performed using the methods provided herein.
Figure 5:
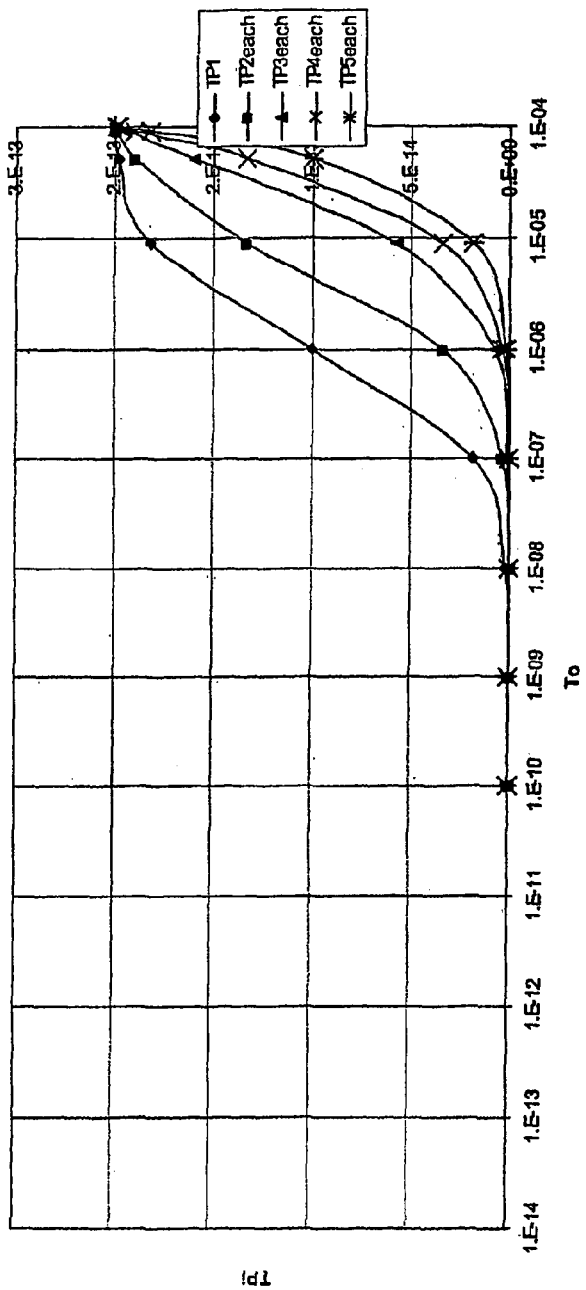
FIG. 5 provides a graph showing bound B-cell concentration verses target concentration. The Figure shows concentration of each bound B-cell binder, TPi, of a library (each member present at a concentration of $1^{-13}$ M) with 1 binder (P1) at Kd=$1^{-10}$ M, 5 binders (P2) at Kd=$5^{-10}$ M, 25 binders (P3) at Kd $2.5^{-9}$ M, 50 binders (P4) at Kd=$5^{-9}$ M, and 100 binders (P5) at Kd=$1^{-8}$ M (and no additional binders). All of the test conditions were the same as indicated in FIG. 4, except that 1 additional competitive non-binder (P6) was present at $1^{-4}$ M ($1^{-8}$ M Kd). The x-axis shows Target concentration (Molar) and the y-axis shows concentration (Molar) of Target-bound member. The Figure shows amount of library member bound as a function of dissociation constant and target concentration for a typical library with members P1 through P5 with one added competitive binder. This Figure is based upon calculations performed using the methods so provided herein.
Figure 6A:
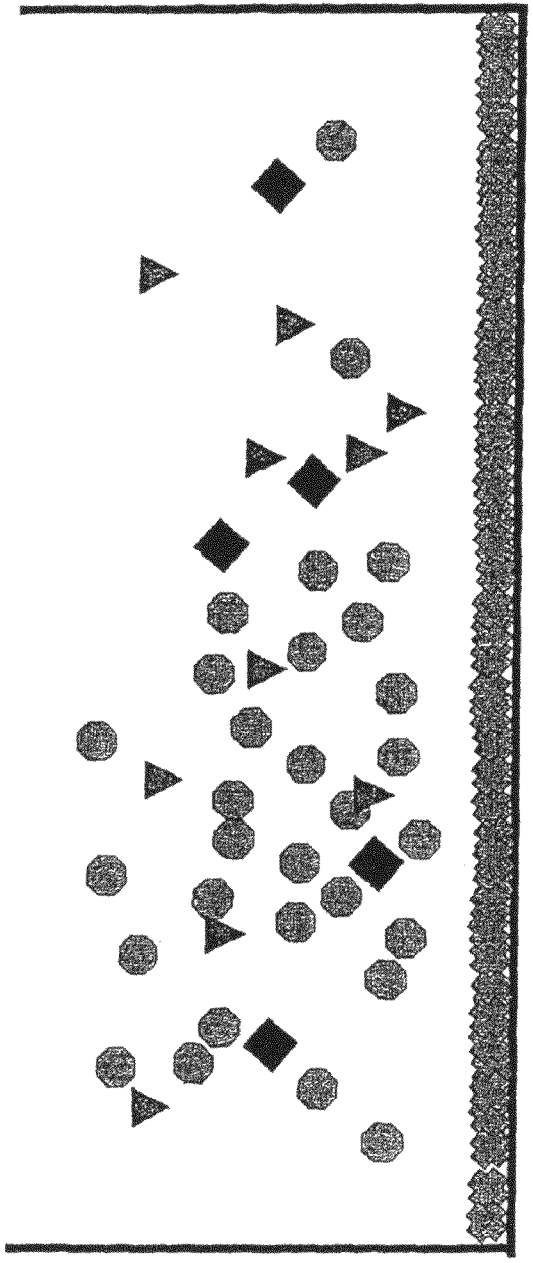
Figure 6B:
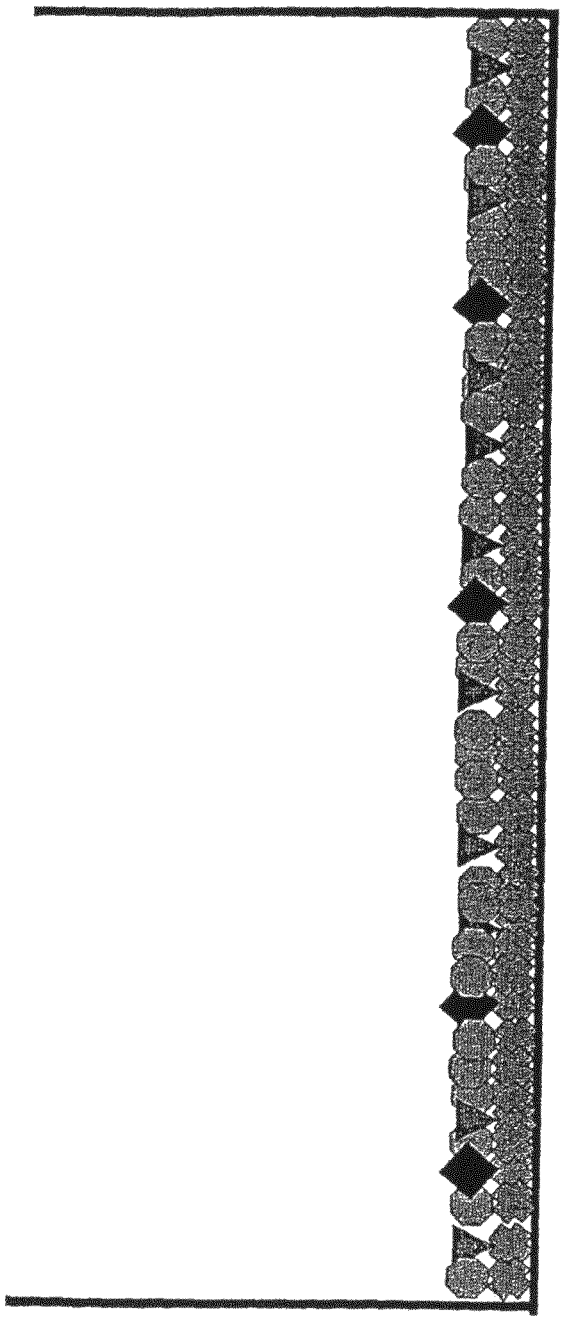
FIG. 6B shows B-cell binders bound to target.
Figure 6C:
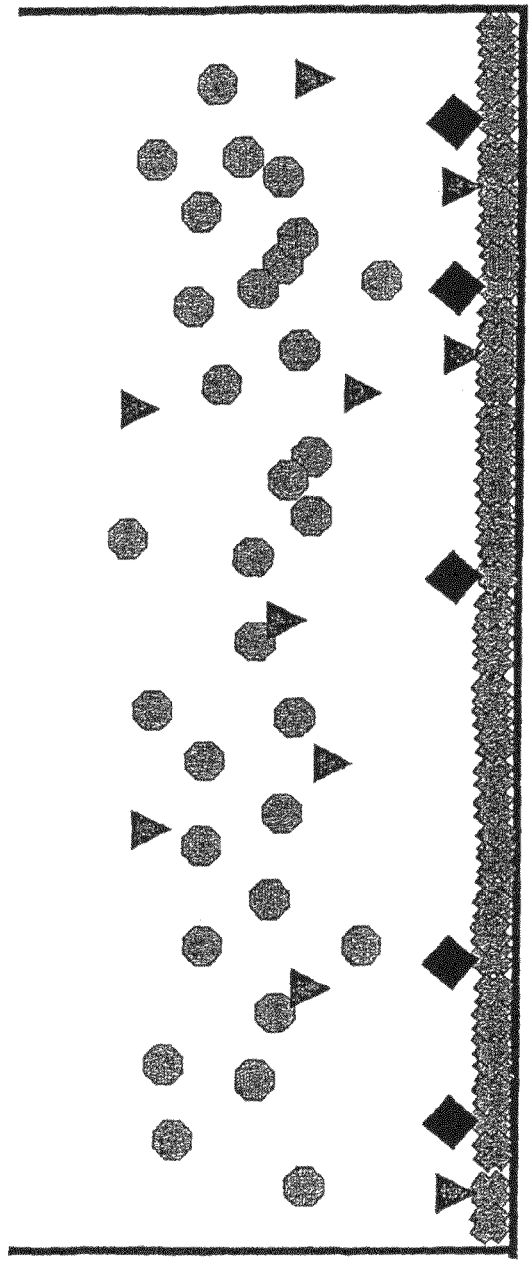
FIG. 6C shows some B-cell binders bound to target. There are three different types of binders represented, and all three take the same amount of time to stick to the target, approximately 10 seconds, but each of the three binders has a different off rate. Binders with a 1 minute off rate are represented by octagons; there are 30 such binders represented. Binders with a 10 minute off rate are represented by a triangle; there are 10 such binders represented. Binders with a 100 minute off rate are represented by a square tilted 45 degrees; there are 5 such binders represented. Target is shown at the bottom of the Figure as an "X.

As $T^o$ approaches 0; $TP_i/TP_1$ approaches $(1) \cdot P_i^o/(1/r_i^1) \cdot P_1^o$ approaches $(r_i^1) \cdot P_i^o/P_1^o$ As $T^o$ approaches ∞; $TP_i/TP_1$ approaches $(x) \cdot P_i^o/(x) \cdot P_1^o$ approaches $P_i^o/P_1^o$ Accordingly, when target is limiting, the amount of each binder relative to the tightest binder is proportional to the ratio of the dissociation constants. When target is at high concentration, each member is bound to the same extent. This relationship is illustrated in FIG. 4. To identify only the tightest binders in a library, the target concentration must be limiting. To identify all binders in a library, the target should be present in excess. The relationship is illustrated in FIG. 5. To increase the proportion of tight binders detected: 1) increase the library concentration; 2) decrease the diversity of library, (increase member concentration); 3) decrease the target concentration; or 4) add an excess of one weak binder that can be distinguished from the other binders (i.e., such that it can be made invisible to the detection system). The relationship is illustrated in FIG. 6.

Example 6

Calculating Mean and Standard Deviations for a B-Cell Library

In this Example, methods to calculate the mean and standard deviation for a B-cell library are provided. To obtain a binder at a desired affinity, the expected mean and standard deviations for the B cell library are calculated based on FACS data. Assuming a binomial distribution of binding energies, the mean and standard deviation of the binding energies in a B-cell library can be estimated by measuring the % of cells that bind as a function of target concentration. Table 2, below, shows these calculations for two unknowns, mean and standard deviation, from the % cells bound at two different target concentrations (e.g., $1\times10^{-9}$M and $5\times10^{-9}$M). If 50% of the cell receptors need to be occupied in order to observe a signal, then the binding energy for each cell observed will be better than or equal to $-12.27$ Kcal/M ($1\times10^{-9}$M) and $-11.32$ Kcal/M ($5\times10^{-9}$M). From as the binomial distribution, the % cells with signal can be used to estimate the number of standard deviations from the mean represented by the binding energy. Thus, there are two equations with two unknowns:

mean$-3.71$ standard deviation$=-12.27$     Equation 1 mean$-3.19$ standard deviation$=-11.32$.     Equation 2

Solving these equations, gives the estimate for the mean and standard deviations for the property (solving for a Factor D binder example):

TABLE 2

Mean and Standard Deviation for Factor D

| Factor D | % Cells with Signal | Calculated Mean and Standard Deviation |
|---|---|---|
| 0 nM | 0 | 0.00% |
| 1 nM | 0.0001 | 0.01%, −3.71 |
| 5 nM | 0.0007 | 0.07%, −3.19 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention should not be unduly limited to such specific embodiments. Indeed, various modifications of the described modes for carrying out the invention which that are obvious to those skilled in molecular biology, assay development, immunology, formulations, and/or related fields are intended to be within the scope of the present invention.

Those skilled in the art readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. Indeed, it is readily apparent to one skilled in the art that varying substitutions and modifications may be made to the invention disclosed herein without departing from the scope and spirit of the invention. The invention illustratively described herein suitably may be practiced in the absence of any element or elements, limitation or limitations that is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

The invention claimed is:

1. A method for isolating human antibodies, comprising:
   a) obtaining B-cells;
   b) purifying said B-cells to provide purified B-cells;
   c) contacting said purified B-cells with at least one labeled target at a number of target concentrations to identify a concentration at which the target concentration is limiting, thereby selecting for purified B-cells that bind tightly to the target;
   d) collecting said B-cells bound to said target; and
   e) distinguishing, separating and identifying the antibody to which said B-cells have bound to said target,
   wherein said at least one labeled target has a target concentration is between about 1 micromolar (1e-6M) and about 1 picomolar (1e-12M).

2. The method of claim 1, wherein the target concentration is between about 1e-7 M and about 1e-11 M.

* * * * *